(12) United States Patent
Matsumoto et al.

(10) Patent No.: US 8,622,108 B2
(45) Date of Patent: Jan. 7, 2014

(54) LABELING MACHINE FOR BLOOD-SAMPLING TUBE AUTOMATIC PREPARATION DEVICE

(75) Inventors: Toshikazu Matsumoto, Yokohama (JP); Yoshimi Hirasawa, Yokohama (JP); Junya Mashiko, Tokyo (JP); Ichiro Nakamura, Kawasaki (JP); Syunji Morishima, Kawasaki (JP)

(73) Assignee: Techno Medica Co., Ltd., Yokohama-shi (JP)

( * ) Notice: Subject to any disclaimer, the term of this patent is extended or adjusted under 35 U.S.C. 154(b) by 44 days.

(21) Appl. No.: 13/376,236

(22) PCT Filed: Jun. 5, 2009

(86) PCT No.: PCT/JP2009/060352
§ 371 (c)(1),
(2), (4) Date: Feb. 23, 2012

(87) PCT Pub. No.: WO2010/140252
PCT Pub. Date: Dec. 9, 2010

(65) Prior Publication Data
US 2012/0138231 A1 Jun. 7, 2012

(51) Int. Cl.
*G05G 15/00* (2006.01)
*B29C 65/48* (2006.01)
*B29C 65/78* (2006.01)
*B32B 41/00* (2006.01)
*B65C 9/46* (2006.01)

(52) U.S. Cl.
USPC ........... 156/351; 156/378; 156/387; 156/537; 156/DIG. 6; 156/DIG. 11; 156/DIG. 13; 156/DIG. 46

(58) Field of Classification Search
USPC ......... 156/350, 351, 378, 384, 387, 537, 538, 156/DIG. 5, DIG. 6, DIG. 8–DIG. 13, DIG. 46
See application file for complete search history.

(56) References Cited

U.S. PATENT DOCUMENTS 3,650,400 A * 3/1972 Warren et al. ................ 250/365
3,954,542 A * 5/1976 Solomon et al. ............. 156/360

(Continued)

FOREIGN PATENT DOCUMENTS

JP 2000-142652 A 5/2000
JP 2001-315729 A 11/2001

(Continued)

OTHER PUBLICATIONS

ISA/JP, International Search Report for international application PCT/JP2009/060352, completed Aug. 18, 2009.

*Primary Examiner* — Sing P Chan
(74) *Attorney, Agent, or Firm* — Stites & Harbison PLLC; Jeffrey A. Haeberlin

(57) ABSTRACT

Provided is a labeling device for an automatic test-tube setting-up device wherein an identification label can be pasted over a product label with a simple structure. A labeling device for an automatic blood-sampling-tube setting-up device comprises a means for taking out a blood-sampling tube based on patient information and supporting the blood-sampling tube at a labeling position, a blood-sampling tube driving means for rotary driving the blood-sampling tube at the labeling position, a label printing means for creating an identification label by printing test information and/or patient information and outputting the identification label to the labeling position, a product label position detecting means for detecting the edge of a product label previously pasted to the outer surface of the blood-sampling tube, and a controller for controlling the operation of the label printing means and the blood-sampling tube driving means such that the identification label is pasted over the product label with a continuous gap left in the axial direction of the blood-sampling tube on the outer surface of a blood-sampling tube based on information about the diameter of a blood-sampling tube corresponding to the blood-sampling tube at the labeling position, and information about the edge of the product label obtained from the product label position detecting means.

9 Claims, 8 Drawing Sheets

(56) References Cited

U.S. PATENT DOCUMENTS

| | | | |
|---|---|---|---|
| 4,657,622 A * | 4/1987 | Paules | 156/361 |
| 4,711,687 A * | 12/1987 | Paules | 156/235 |
| 5,725,719 A * | 3/1998 | Szczepaniec et al. | 156/353 |
| 5,846,005 A * | 12/1998 | Britz et al. | 400/621 |
| 6,172,688 B1 * | 1/2001 | Iwasaki et al. | 347/2 |
| 6,309,724 B1 * | 10/2001 | Kulper et al. | 428/40.1 |
| 6,357,941 B1 * | 3/2002 | Amano et al. | 60/761 |
| 6,432,235 B1 * | 8/2002 | Bleckmann et al. | 156/73.1 |
| 6,780,265 B2 * | 8/2004 | Bleckmann et al. | 156/73.1 |
| 6,793,755 B2 * | 9/2004 | Schaupp et al. | 156/215 |
| 6,827,817 B2 * | 12/2004 | Bleckmann et al. | 156/73.1 |
| 6,830,639 B2 * | 12/2004 | Bleckmann et al. | 156/73.3 |
| 7,478,956 B2 * | 1/2009 | Sanbongi et al. | 400/611 |
| 8,179,900 B2 * | 5/2012 | Kitada | 370/395.53 |
| 8,410,912 B2 * | 4/2013 | Kojima | 340/10.52 |
| 8,436,734 B2 * | 5/2013 | Kato et al. | 340/572.8 |
| 2002/0176730 A1 * | 11/2002 | Bleckmann et al. | 400/615.2 |
| 2002/0185212 A1 * | 12/2002 | Schaupp et al. | 156/205 |
| 2002/0189750 A1 * | 12/2002 | Bleckmann et al. | 156/176 |
| 2004/0026919 A1 * | 2/2004 | Bleckmann et al. | 283/81 |
| 2004/0238098 A1 * | 12/2004 | Bleckmann et al. | 156/73.1 |
| 2004/0247832 A1 * | 12/2004 | Koops et al. | 428/156 |
| 2005/0139325 A1 * | 6/2005 | Bleckmann et al. | 156/510 |
| 2005/0241200 A1 * | 11/2005 | Hsu | 40/638 |
| 2006/0082637 A1 * | 4/2006 | Sanbongi et al. | 347/213 |
| 2006/0096710 A1 * | 5/2006 | Tsukamoto et al. | 156/384 |
| 2007/0023516 A1 * | 2/2007 | Chapman et al. | 235/432 |
| 2008/0025778 A1 * | 1/2008 | Ito et al. | 400/76 |
| 2008/0031672 A1 * | 2/2008 | Yamaguchi et al. | 400/76 |
| 2008/0189059 A1 * | 8/2008 | Choong et al. | 702/57 |
| 2008/0232886 A1 * | 9/2008 | Kato et al. | 400/76 |
| 2008/0290648 A1 * | 11/2008 | Koops et al. | 283/81 |
| 2009/0167013 A1 * | 7/2009 | Horikoshi | 283/81 |
| 2009/0237221 A1 * | 9/2009 | Battles et al. | 340/10.51 |
| 2010/0188244 A1 * | 7/2010 | Sattler et al. | 340/686.1 |
| 2010/0189115 A1 * | 7/2010 | Kitada | 370/400 |
| 2010/0245058 A1 * | 9/2010 | Kojima | 340/10.52 |
| 2011/0146912 A1 * | 6/2011 | Howarth et al. | 156/350 |
| 2013/0011629 A1 * | 1/2013 | Brandon et al. | 428/192 |

FOREIGN PATENT DOCUMENTS

| | | |
|---|---|---|
| JP | 2002-340910 A | 11/2002 |
| JP | 2008-037464 A | 2/2008 |
| JP | 2008-302934 A | 12/2008 |

* cited by examiner

LABELING MACHINE FOR BLOOD-SAMPLING TUBE AUTOMATIC PREPARATION DEVICE

FIELD OF THE INVENTION

The present invention relates to an improvement of a labeling machine used for blood-sampling tube automatic preparation device that automatically prepares one or more blood-sampling tubes for every patient before collecting blood.

BACKGROUND ART

Conventionally, in order to automatically prepare efficiently and reliably one or more blood-sampling tubes for every patient before collecting blood, a blood-sampling tube automatic preparation device have already been proposed. The preparation device, based on information related to one patient including examination information and patient information or the like, automatically selects a blood-sampling tube required to an examination for the patient, prints the examination information and a patient ID or the like corresponding to the patient on a label to make an identification label, automatically pastes the identification label on an outer surface of the selected blood-sampling tube, and then collects one or more blood-sampling tube on which the identification label is pasted for each patient into a tray (Patent documents 1 to 3).

The information printed on the label that is pasted on the blood-sampling tube is used in order that a worker may compare the patient and the blood-sampling tube in a blood sampling room. Also said information printed on the label is used in order that an automatic analyzer may identify the blood-sampling tube containing blood.

By the way, a production label L2 is pre-pasted on some vacuum type blood-sampling tubes (a) (See FIG. 9(a)). The name of the manufacturer and type of vacuum type blood-sampling tubes are printed on said production label L2.

If the identification label L is easily pasted on such the vacuum type blood-sampling tube (a) with the product label L2, the identification label L and the product label L2 may cover all the external surface of the blood-sampling tube (a) (See FIG. 9(b)).

If the labels L and L2 cover all the external surface of the blood-sampling tube, it becomes impossible for the worker to see the quantity of the blood in the blood-sampling tube during the blood collecting process. In the blood examination, blood collected in one blood-sampling tube may not only be used for one kind of inspection, but may also be used for two or more kinds of inspections. Therefore, the quantity of the blood collected in the blood-sampling tube always is not the same. According to the purpose of the inspection, or the kind of blood-sampling tube, the quantity of the blood to be collected in the blood-sampling tube must be changed. But as described above, if the labels L and L2 cover all the external surface of the blood-sampling tube (a), it is very difficult to check the quantity of the blood in the blood-sampling tube by the worker during the blood collecting process.

The blood-sampling tube is transferred to an automatic analyzer that conducts a blood analysis. As described above, if the labels L and L2 cover all the external surface of the blood-sampling tube (a), the automatic analyzer cannot automatically measure the quantity of the blood within the blood-sampling tube (a).

In order to solves the above problem related to the identification label L and the production label L2 pasted on the outer surface of the blood-sampling tube, in the Patent document 4 a labeling machine has been proposed. Before pasting the identification label, said labeling machine detects a position of the production label pre-pasted on the blood-sampling tube, and pastes an identification label above the production label so as to overlap the identification label on the production label, so that after pasting the identification label, the identification label and the production label may not cover all the external surface of the blood-sampling tube (See Patent document 4).

PATENT DOCUMENTS

[Patent Document 1] Japanese Patent No. 2834595
[Patent Document 2] Japanese Patent No. 2871502
[Patent Document 3] Japanese Patent No. 3070522
[Patent Document 4] Japanese Patent Kokai 2008-302934

DISCLOSURE OF THE INVENTION

Problems to be Solved by the Invention

Said labeling machine described in the Patent Document 4 comprises a production label position detecting sensor for detecting an edge of the production label pre-pasted on the blood-sampling tube and an identification label position detecting sensor for detecting a leading edge of the identification label supplied from a label supply, which is arranged near the outer surface of the blood-sampling tube, and on the basis of the detected position signals from the these sensors controls a timing of the rotating the blood-sampling tube and a timing of the supplying the identification label to the blood-sampling tube, such that the identification label will be pasted over the production label so as to not cover all the external surface of the blood-sampling tube by the labels.

By the above mentioned composition, the production label and the identification label doesn't cover all the external surface of the blood-sampling tube.

However, there is a problem that the labeling machine according to the Patent Document 4 described above needs two additional sensors (i.e. the production label position detecting sensor and the identification label position detecting sensor) to suitably paste the identification label.

As described above, since the labeling machine disclosed in the Patent Document 4 comprises two additional sensors, the structure of the labeling machine becomes complicated and a manufacturing cost also becomes high. In particular, since the identification label position detecting sensor is intended to use for detecting the leading edge of the identification label supplied from the label supply, it is necessary to arrange the sensor between the label supply and the blood-sampling tube with which the identification label is pasted. However in order to arrange the sensor between the label supply and the blood-sampling tube with which the identification label is pasted, it is necessary to make the interval between the label supply and the blood-sampling tube with which the identification label is pasted large. Thereby, the problem that the labeling machine will be enlarged arises.

If the production label position detecting sensor for detecting the edge of the production label is arranged such that it detects the edge of the production label at a label pasting starting position at which the identification label begins to be pasted on the blood-sampling tube, when the sensor detects the edge of the production label, rotation of the blood-sampling tube is stopped, and the label is supplied to the label pasting starting position, so that it is possible to paste the identification label on the production label. However since the label pasting starting position is near the top of a label pasting roller it is impossible to arrange the production label position detecting sensor such that it detect the edge of the production label at the label pasting starting position. Therefore, in the prior labeling machine, the production label position detecting sensor detects the edge of the production label at a position apart from the label pasting starting position. And then in the labeling machine, the rotation movement timing of the blood-sampling tube and the supplying movement timing for supplying the identification label to the blood-sampling tube are controlled such that when the edge of the production label reaches at the label pasting starting position the leading edge of the identification label reaches at the label pasting starting position.

By the way, the diameters of the blood-sampling tubes differ according to the use or the kind of the blood-sampling tube. If a diameter of one blood-sampling tube differs from a diameter of the another blood-sampling tube, that is, two blood-sampling tube have different diameters to each other, the distance between the position at which the edge of the production label is detected and the label pasting starting position of the one blood-sampling tube differs from the distance between the position at which the edge of the production label is detected and the label pasting starting position of the other blood-sampling tube. Therefore, the distance which rotates the one blood-sampling tube to move the edge of the production label to the label pasting starting position differs from the distance which rotates the other blood-sampling tube to move the edge of the production label to the label pasting starting position.

However, in the labeling machine described in the Patent Document 4, nothing is taken into consideration about the difference of the diameters among blood-sampling tubes. Therefore, in the labeling machine described above, if the diameter of the blood-sampling tube differs from the predetermined reference value related to the diameter of the blood-sampling tube, it is impossible to paste the identification label over the production label so as not to cover all the external surface of the blood-sampling tube by the labels.

Inventors came to invent the present invention, in order to find out the above-mentioned conventional problem and to solve this.

It is an object of the present invention to solve the above-mentioned problems and provide the labeling machine for blood-sampling tube automatic preparation device that has easy structure and can paste the identification label on the production label.

Means of Solving the Problem

To achieved the above object, the labeling machine for blood-sampling tube automatic preparation device according to the present invention, which selectively automatically picks up a blood-sampling tube required for the examination of the patient from blood-sampling tube containing sections on the basis of an information related to one patient that includes the examination information and/or patient information, prints the examination information and/or patient information on a label on the basis of said information related to one patient so as to make an identification label, pastes the identification label on the blood-sampling tube picked up from the blood-sampling tube containing sections, and collects the blood-sampling tube on which the identification label is pasted into a container for every patient, characterized in that said labeling machine comprises a supporting means for supporting the blood-sampling tube that is picked up on the basis of the information related to one patient at a label pasting position, a blood-sampling tube driving means for rotating the blood-sampling tube at the label pasting position, a label printing means for printing the examination information and/or the patient information on the label on the basis of the information related to one patient to make an identification label and for outputting the identification label to the label pasting position, a production label position detection means for detecting an edge of a production label pre-pasted on the surface of the blood-sampling tube at the label pasting position, and a control means for controlling the operations of the label printing means and the blood-sampling tube drive means so as to paste the identification label on the production label remaining a clearance gap continuously extended along the axis direction of the blood-sampling tube on the surface of the blood-sampling tube on the basis of a diameter information of the blood-sampling tube at the label pasting position and the edge information of the production label detected by the production label position detection means.

Although said control means may be a controller only for the labeling machine, it may be a controller which controls operation of the whole blood-sampling tube automatic preparation device.

Said control means may include a memory in which diameter information for each of the blood-sampling tubes is stored.

Also said control means may receive the diameter information for each of the blood-sampling tubes from a host computer.

Furthermore, the labeling machine according to the present invention may comprise a measuring means for measuring the diameter of the blood-sampling tube at the label pasting position. In this case, said control means may receive the diameter information for each of the blood-sampling tubes from the measuring means.

In case that the labeling machine comprises a bar-code reader for checking the identification label pasted on the blood-sampling tube, the bar-code reader may be intended to use as the production label detection means.

Effect of the Invention

As described above, in the labeling machine for blood-sampling tube automatic preparation device according to the present invention, it selectively automatically picks up a blood-sampling tube required for the examination of the patient from blood-sampling tube containing sections on the basis of an information related to one patient that includes the examination information and/or patient information, prints the examination information and/or patient information on a label on the basis of said information related to one patient so as to make an identification label, pastes the identification label on the blood-sampling tube picked up from the blood-sampling tube containing sections, and collects the blood-sampling tube on which the identification label is pasted into a container for every patient. And the labeling machine according to the present invention is characterized in that it comprises a supporting means for supporting the blood-sampling tube that is picked up on the basis of the information related to one patient at a label pasting position, a blood-sampling tube driving means for rotating the blood-sampling tube at the label pasting position, a label printing means for printing the examination information and/or the patient information on the label on the basis of the information related to one patient to make an identification label and for outputting the identification label to the label pasting position, a production label position detection means for detecting an edge of a production label pre-pasted on the surface of the blood-sampling tube at the label pasting position, and a control means for controlling the operations of the label printing means and the blood-sampling tube drive means so as to paste the identification label on the production label remaining a clearance gap continuously extended along the axis direction of the blood-sampling tube on the surface of the blood-sampling tube on the basis of a diameter information of the blood-sampling tube at the label pasting position and the edge information of the production label detected by the production label position detection means. Therefore, in the labeling machine according to the present invention it is not necessary to arrange an additional sensor for detecting the leading edge of the pre-printed identification label supplied from the label supply, so that it is not necessary to make the interval space between label supply and the blood-sampling tube at the label pasting position. As described above, since the labeling machine according to the present invention does not need the additional sensor, the labeling machine according to the present invention is simple for the structure thereof and the size thereof is also small.

Also, the labeling machine according to the present invention controls the movements of the label supply and blood-sampling tube driving means on the basis of the information related to the diameter of the blood-sampling tube and the information related to the position of the edge of the production label. Thereby the labeling machine according to the present invention may always paste the identification label correctly according to the size of the diameter of the blood-sampling tube.

MODE FOR CARRYING OUT THE INVENTION

A labeling machine for blood-sampling tube automatic preparation device according to the present invention will be described in further detail with reference to the accompanying drawings that illustrate some embodiments.

Figure 1:
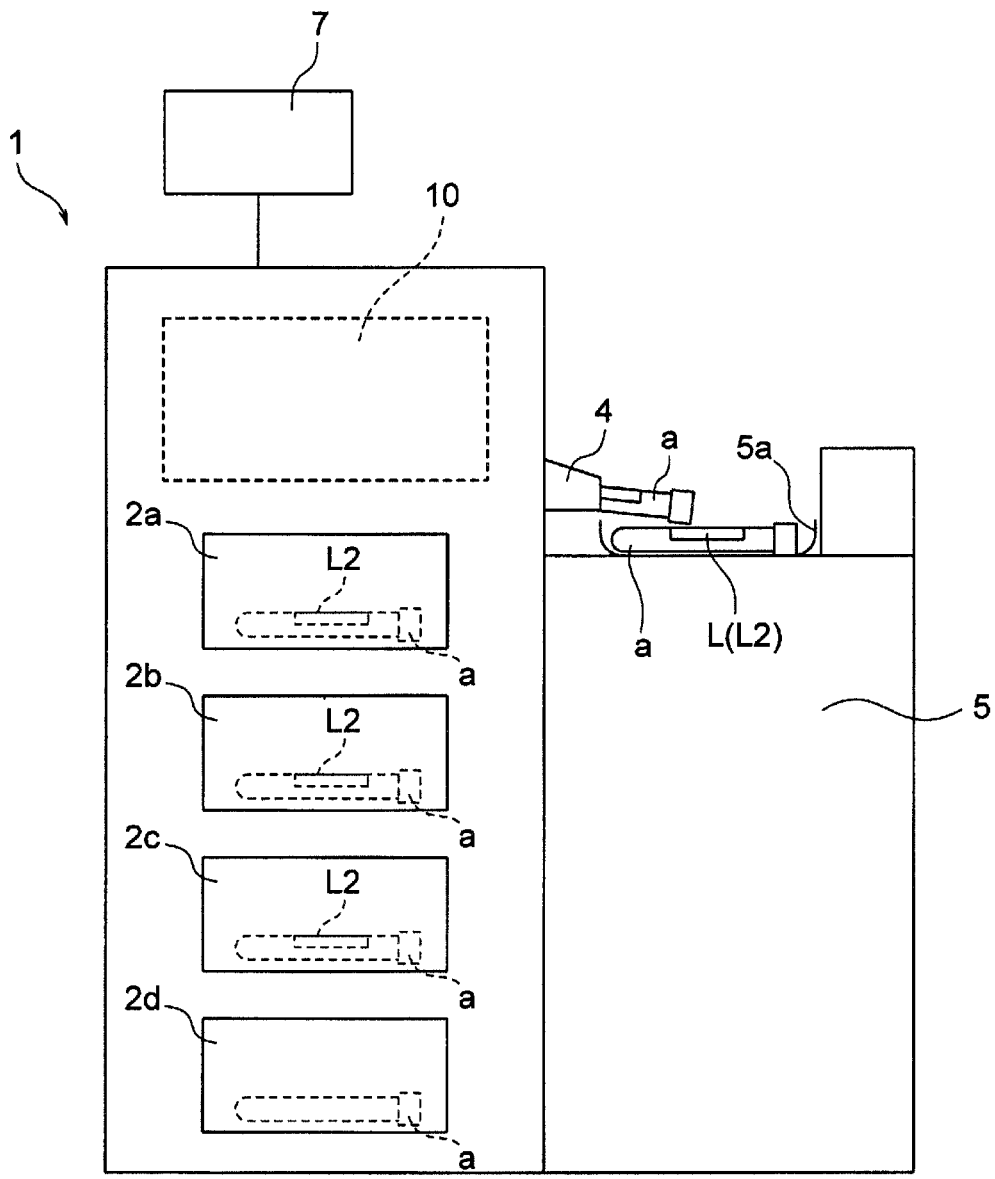
FIG. 1 is a schematic front view of a blood-sampling tube automatic preparation system.

FIG. 1 is a schematic front view of a blood-sampling tube automatic preparation system.

In the FIG. 1, reference numeral 1 indicates a blood-sampling tube automatic preparation device.

The blood-sampling tube automatic preparation device 1 comprises a plurality of blood-sampling tube containing sections 2 (2a~2d), each of the sections 2 being intended to contain same kind of blood-sampling tubes (a: a1~a4), and a transferring means (not shown in the figure) for selectively picking up the blood-sampling tube (a) from the containing sections 2 and transferring the blood-sampling tube to a label pasting position.

The blood-sampling tube automatic preparation device 1 also comprises a labeling machine 10 according to the present invention that is arranged at the label pasting position of the automatic preparation device 1.

The labeling machine 10 makes an identification label L by printing examination information and/or patient information in the form of a bar-code and characters on a label on the basis of information related to one patient corresponding to the blood-sampling tube (a) being transferred by the transferring means. Then the labeling machine 10 pastes said identification label L on the surface of the said blood-sampling tube (a) along the axis direction thereof.

In this specification, the examination information may be for example information about the kind of inspection which a patient should undergo and the patient information may be for example a patient ID number, a patient name and/or a blood sampling receipt number.

The blood-sampling tube (a) on which the identification label L has been pasted is transferred to an outlet 4 by a discharge means not shown in Figure (that may be for example a belt conveyer or the like) and is discharged from the blood-sampling tube automatic preparation device 1 through the outlet 4 to a collection means 5.

The collection means 5 has a plurality of containing means 5a such as trays or bags, and each of the containing means 5a is intended to contain all the blood-sampling tubes used for collecting blood of one patient.

As described above, in the blood-sampling tube automatic preparation system, the blood-sampling tube(s) required for a patient' blood collecting is automatically selected, and on the selected tube is pasted the label on which the necessary information is printed, and then the tube with the label pasted is put in the tray for every patient.

Hereinafter the construction of the labeling machine according to the present invention will be described in detail.

Figure 2:
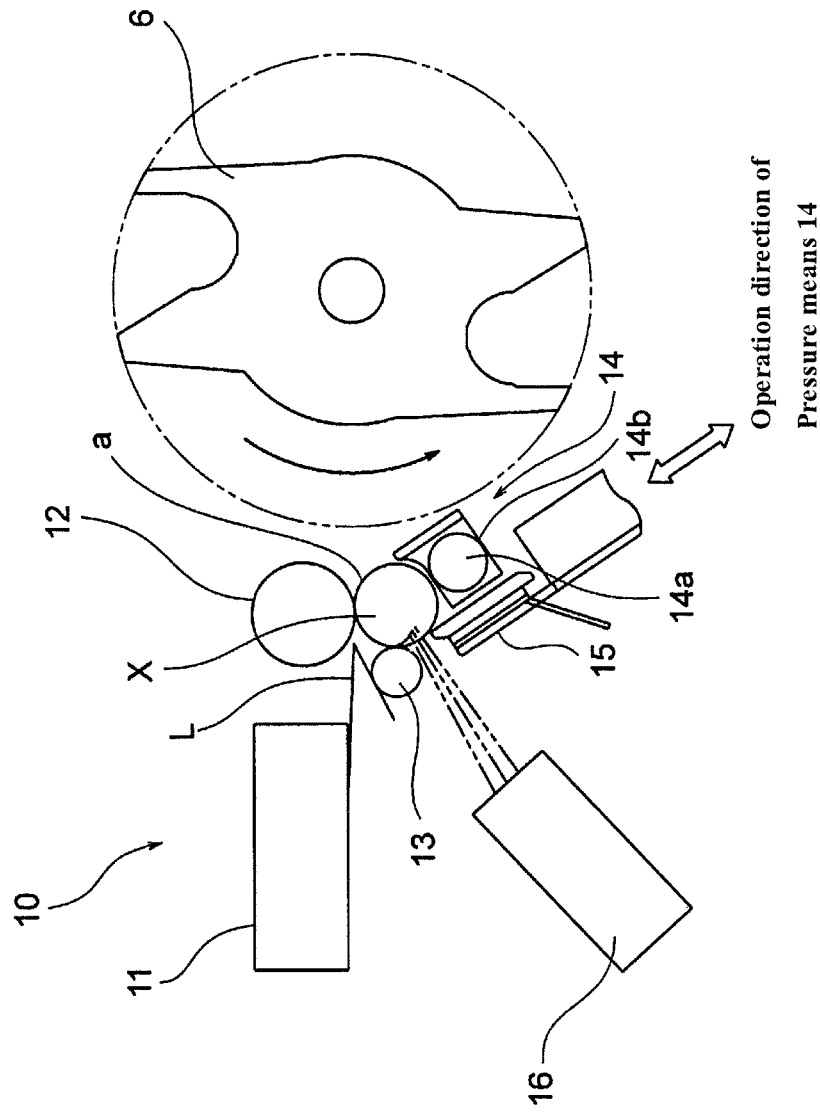
FIG. 2 schematically shows an embodiment of the labeling machine.

FIG. 2 schematically shows the configuration of the labeling machine 10.

In FIG. 2, reference numeral 6 is a blood-sampling tube supplying means which supplies the blood-sampling tube transferred by the transferring means not shown to the labeling machine 10.

As shown FIG. 2, the labeling machine 10 comprises a label printer 11, a driving roller 12, a support roller 13, a pressure means 14, a guide part 15 and a bar-code reader 16. The driving roller 12, the support roller 13 and the pressing means 14 define the label-pasting position X.

Said label printer 11 prints the examination information and/or patient information in the form of the bar-code and characters on the label to make the identification label L on the basis of the information related to one patient corresponding to the blood-sampling tube (a) transferred into the label-pasting position X.

The identification label L made by the label printer 11 is transferred toward the area between the blood-sampling tube (a) and the driving roller 12 in the label-pasting position X.

The pressure means 14 has a pressure roller 14a and a pressure rack 14b for moving reciprocally the pressure roller 14a toward the label-pasting position X. Before the blood-sampling tube (a) is supplied from the blood-sampling tube supplying means 6, the pressure rack 14b is retreated, i.e. the pressure rack 14b is moved in the direction away from the label-pasting position X. When the blood-sampling tube (a) is supplied from the blood-sampling tube supplying means 6, the pressure rack 14b is advanced, i.e. the pressure rack 14b is moved in the direction approaching the label-pasting position X so that the pressure rack 14b presses the blood-sampling tube (a) against the driving roller 12.

The position in which the blood-sampling tube (a) is pressed against the driving roller 12 by the pressure means 14 is the label-pasting position X. In the label-pasting position X, the blood-sampling tube (a) is supported by the three point with the driving roller 12, the supporting roller 13 and the pressure roller 14a.

The operations of the label printer 11, driving roller 12, pressure means 14, bar-code reader 16 and blood-sampling tube supplying means 6 are controlled by a main controller 7. The main controller 7 also controls the operation of the blood-sampling tube automatic preparation device 1.

The bar-code reader 16 is intended for reading the barcode printed on the identification label L pasted on the blood-sampling tube (a) and checking whether said barcode printed on the identification label L is correct or not. In this embodiment, the bar-code reader 16 is also intended for detecting an edge of a production label L2 (FIGS. 1 and 3) pre-pasted on the blood-sampling tube (a).

Figure 3:
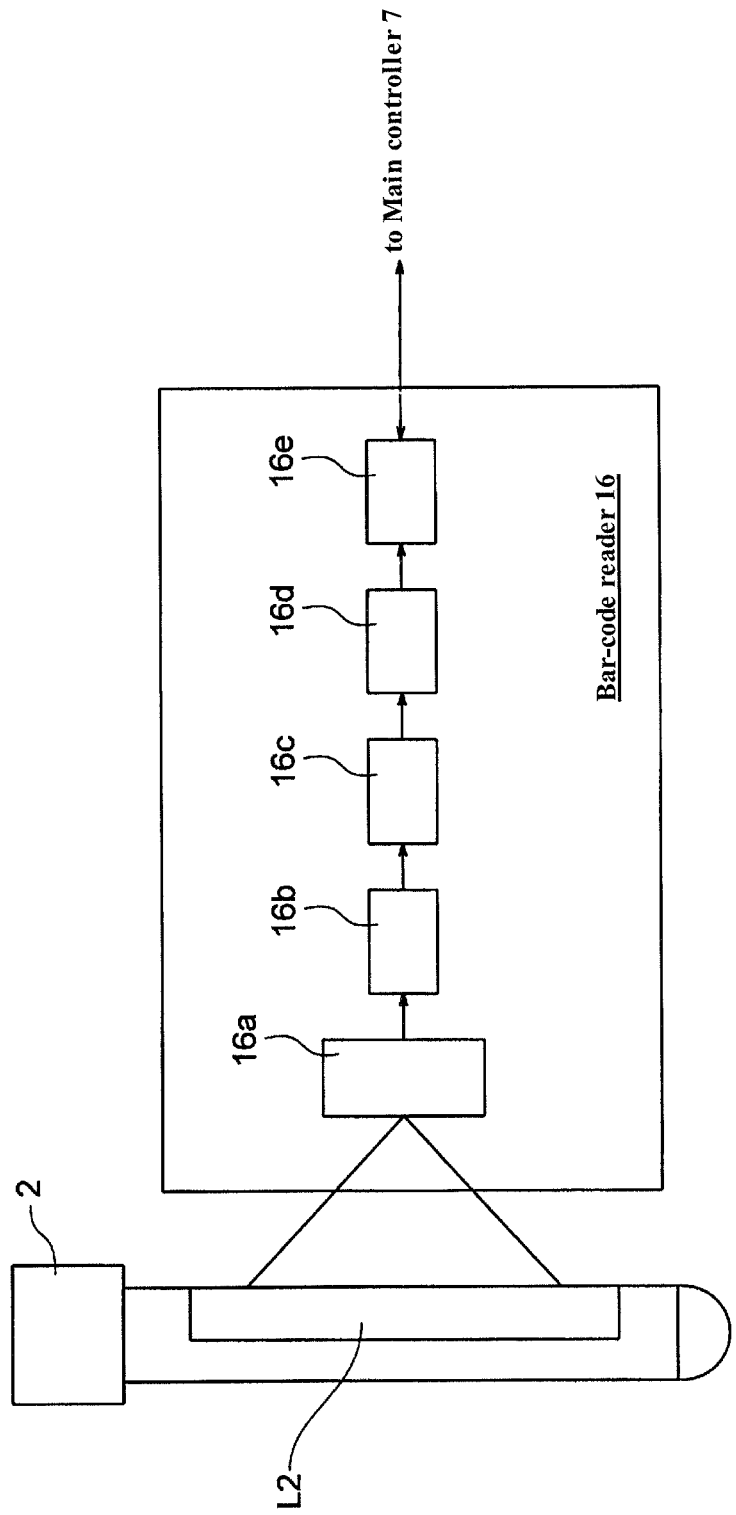
FIG. 3 is a schematic block diagram showing an embodiment of the bar-code reader.
Figure 4:
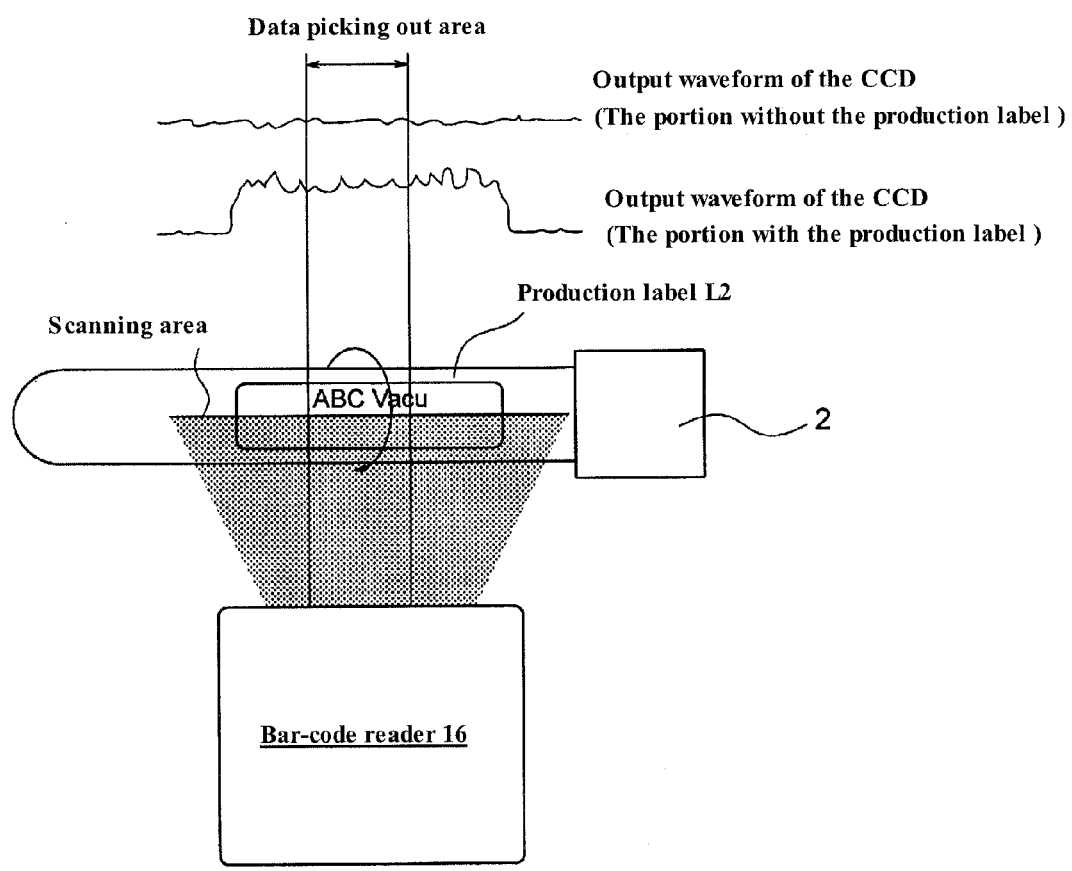
FIG. 4 schematically shows the edge detection process by the bar-code reader.

FIG. 3 is a schematic block diagram showing the framework in relation to an edge detection function of the bar-code reader 16. FIG. 4 schematically shows the edge detection process by the bar-code reader 16.

As shown in the drawings, the bar-code reader 16 comprises a CCD 16a, a low-pass filter 16b, a sampling and holding circuit 16c, an A/D converter 16d and a CPU 16e.

The bar-code reader 16 scans an external surface of the blood-sampling tube (a) several times along the longitudinal direction thereof by means of the CCD 16a to detect a reflection ratio of the external surface of the blood-sampling tube (a) while the blood-sampling tube (a) is rotated at the label-pasting position X by means of the driving roller 12.

The driving roller 12 rotates the blood-sampling tube (a) for one turn about the center axis thereof on the basis of the diameter of the blood-sampling tube (a).

The output signal of the CCD 16a is transmitted to the sampling and holding circuit 16c through the low-pass filter circuit 16b. And then the sampling and holding circuit 16c picks out the signal corresponding to a data picking out area information from the signal transmitted from the low-pass filter circuit 16b.

In this specification, a data picking out area is a data area suitable for detecting the production label L2 among the signal which is obtained by CCD 16a. And the data picking out area information is a signal representing the data picking out area. For example the data picking out area may be an area corresponding to a central area of the production label L2. The data picking out area may be determined suitably beforehand and stored in a host controller, for example, the main controller 7 of the blood-sampling tube automatic preparation device 1 or a host computer connected to the blood-sampling tube automatic preparation device 1. In this case, the CPU 16e of the bar-code reader 16 receives the data picking out area information from the host controller. Alternatively, the data picking out area may be automatically determined by the CPU 16e on the basis of the signal that is obtained by the CCD 16a. In this case, CPU 16e detects an area where a white level is high among the signal obtained by scanning the external surface of the blood-sampling tube (a) several times along the longitudinal direction thereof by means of the CCD 16a and selects the area having the high white level as the data picking out area.

The A/D conversion of the signal sampled and held by the sampling and holding circuit 16c is carried out on the basis of the predetermined suitable threshold level at suitable timing by the A/D converter 16d, and the digital signal are sent to the CPU 16e.

The A/D conversion may be carried out for all signal of area (all of the pixels) sampled and held. Alternatively the A/D conversion may be carried out only for predetermined area.

The CPU 16e receives the digital signal from the A/D converter, calculates the mean or average of the digital signal, and stores the calculated data as one data.

Therefore, the CPU 16e stores one data for every scanning. For example if the CCD 16a scans the external surface of the blood-sampling tube along the longitudinal direction thereof at intervals of 2 milliseconds and the driving roller 12 rotates the blood-sampling tube such that the blood-sampling tube may go around for a period of 400 milliseconds, the number of data to be stored in the CPU 16e will be two hundreds.

The CPU 16e detects an edge of the production label on the basis of a data row which contains data for one turn of the blood-sampling tube.

Figure 5:
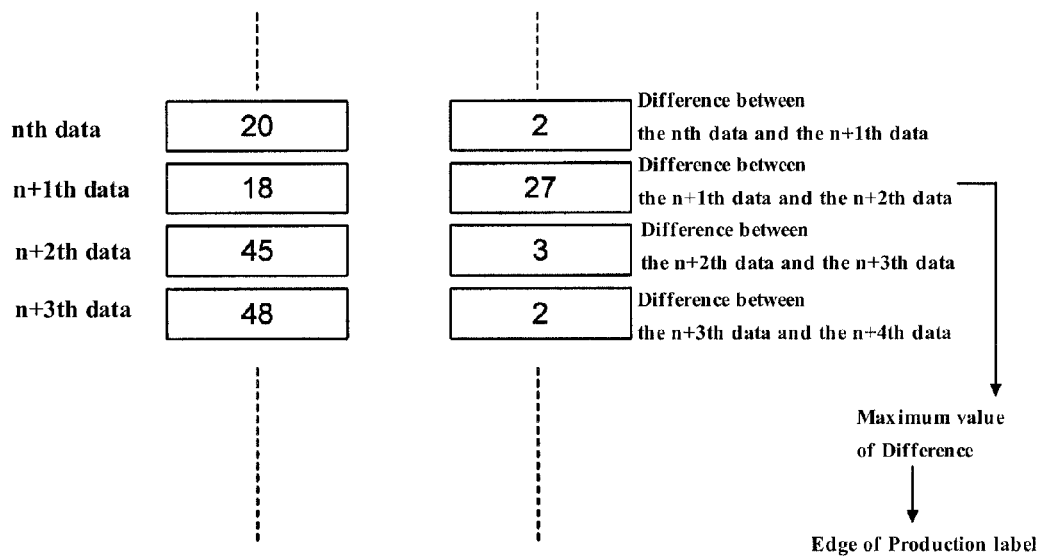
FIG. 5 schematically shows an embodiment of the edge detection method by means of the CPU of the bar-code reader.

The edge of the production label may be detected by various methods. For example, as shown in FIG. 5, the CPU 16e may calculate each of differences between two continuous data of the data row which contains data for one turn of the blood-sampling tube, and may detect the position corresponding to two continuous data in which the difference becomes the maximum as an edge of the production label.

The information related to the edge of the production label detected by the bar-code reader 16 is transmitted to the main controller 7.

Figure 9:
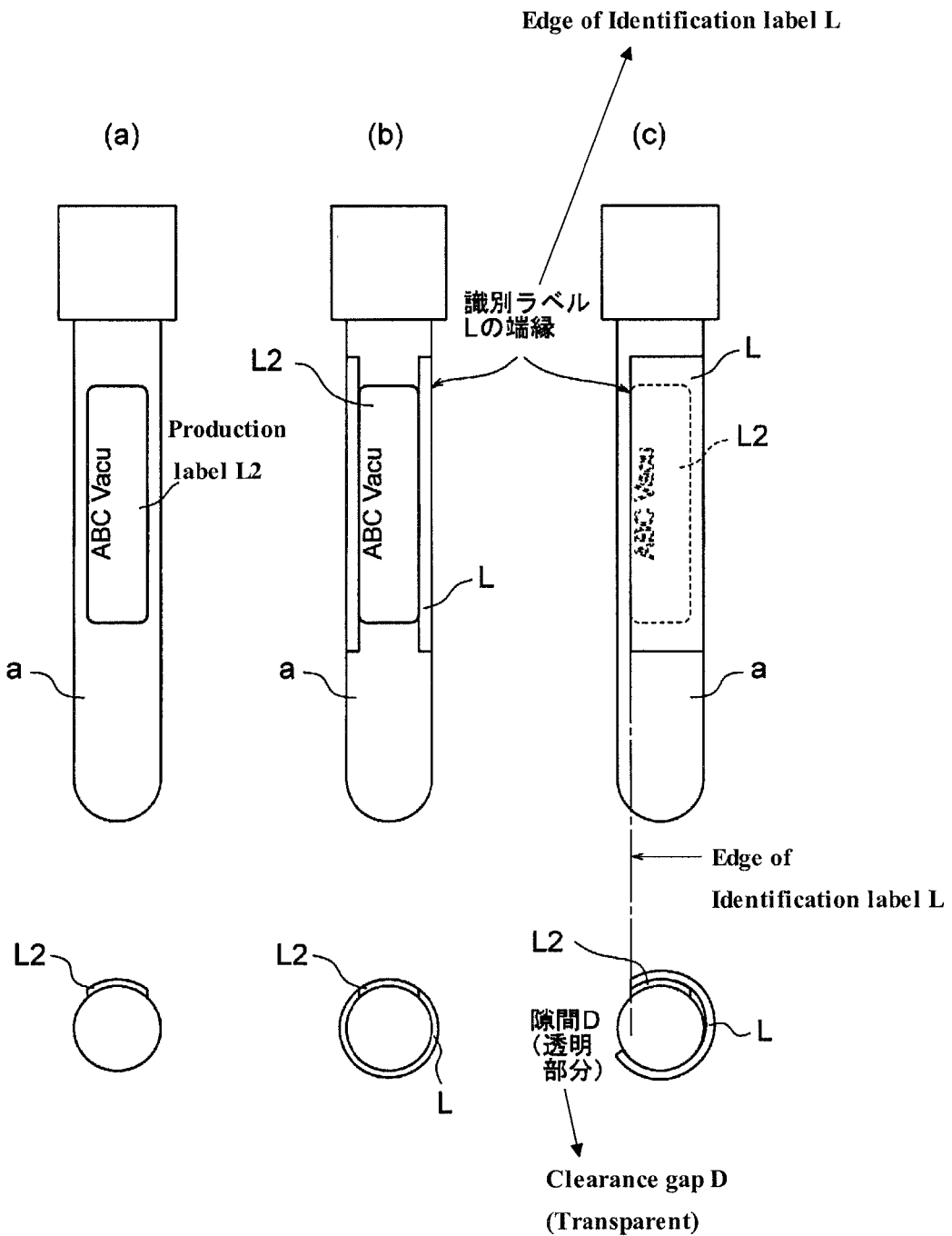
FIG. 9(a) shows a vacuum type blood-sampling tube on which the production label is pre-pasted.
FIG. 9(b) shows a vacuum type blood-sampling tube on which the identification label is pasted so that the identification label and the pre-pasted production label cover all the external surface of the blood-sampling tube.
FIG. 9(c) shows a vacuum type blood-sampling tube on which the identification label is pasted by means of the labeling machine according to the present invention.

The main controller 7 controls the operation of the driving roller 12 such that the leading edge of the label L continuously supplied by the label printer 11 is matched with the edge of the production label L2 and the identification label L is superposed on the production label L2 on the basis of the information related to the diameter of the blood-sampling tube (a) positioned in the label pasting position X and the information related to the edge of the production label detected by the bar-code reader 16. Thereby, after pasting the identification label L, the identification label L is superposed on the production label L2, the identification label L and the production label L2 does not cover all the external surface of the blood-sampling tube (a), a clearance gap D continuous in the direction of the axis of the blood-sampling tube remains in the external surface of the blood-sampling tube, and visibility is secured (See FIG. 9(c)).

In this disclosure, the information related to the diameter of the blood-sampling tube may be pre-stored in the main controller 7 or the host computer connected with the blood-sampling tube automatic preparation device 1.

For example, the main controller 7 may be provided with a memory (not shown in figure) and each of the information related to the diameters of the blood-sampling tubes contained in the each container 2 may be pre-stored in the memory.

Alternatively, a sensor for detecting the diameter of the blood-sampling tube positioned in the label pasting position X may be provided near the label pasting position X, and the main controller 7 may get the information related to the diameter of the blood-sampling tube from the sensor.

Next, another embodiment of the method for detecting the information related to the edge of the production label by the bar-code reader will be described.

In this embodiment as well as the above mentioned embodiment, the bar-code reader 16 scans the external surface of the blood-sampling tube several times along the longitudinal direction thereof by mean of the CCD 16a while the blood-sampling tube is rotated at the label-pasting position X, the sampling and holding circuit 16c picks out the signal corresponding to the data picking out area information from the signal obtained by the CCD 16a, the A/D conversion is carried out for the picked out signal on the basis of the predetermined suitable threshold level, and then the digital signals are stored in the CPU 16e.

Figure 6:
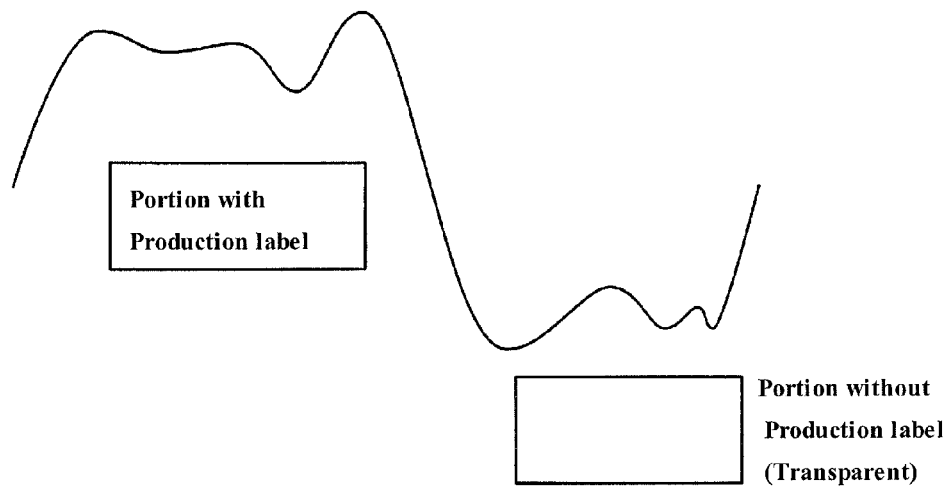
FIG. 6 shows the data obtained by adding the data for one round of a blood sampling tube in the main scanning direction.
Figure 7:
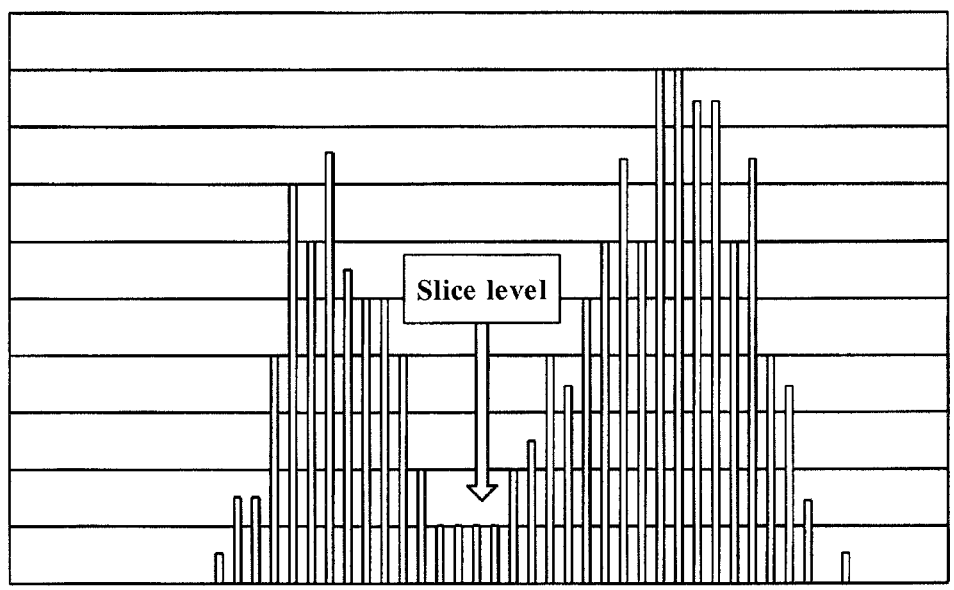
FIG. 7 shows a histogram of the data shown in FIG. 6.

The CPU 16e receives the digital signals from the A/D converter 16d, and adds the signals in the main scanning direction for one round of a blood sampling tube (See FIG. 6) to make the histogram thereof (See FIG. 7).

As shown in FIG. 7, in the above mentioned histogram, there are two peaks, one corresponds to the production label area and the other corresponds to the transparent area (other than the production label area). CPU 16e detects the intermediate point between the two peaks as the information related to the edge of the production label L2 and outputs the information related to the edge of the production label to the main controller 7.

The main controller 7 controls the operation of the driving roller 12 such that the edge of the label L continuously supplied by the label printer 11 is matched with the edge of the production label L2 on the basis of the information related to the diameter of the blood-sampling tube (a) positioned in the label pasting position X and the information related to the edge of the production label detected by the bar-code reader 16.

Next, further another embodiment of the method for detecting the information related to the edge of the production label by the bar-code reader will be described.

In this embodiment as well as the above mentioned embodiment, the bar-code reader 16 scans the external surface of the blood-sampling tube several times along the longitudinal direction thereof by mean of the CCD 16a while the blood-sampling tube is rotated at the label-pasting position X, the sampling and holding circuit 16c picks out the signal corresponding to the data picking out area information from the signal obtained by the CCD 16a, the A/D conversion is carried out for the picked out signal on the basis of the predetermined suitable threshold level, and then the A/D converted or digital signals are stored in the CPU 16e.

The CPU 16e receives the digital signals from the A/D converter 16d, calculates the means of the all signals for the blood-sampling tube round, and sets the means value as a slice level.

The bar-code reader 16 also scans the external surface of the blood-sampling tube along the longitudinal direction thereof by means of the CCD 16a while the driving roller 12 rotates the blood-sampling tube (a) to paste the production label L, and transmits the scanned signal to the CPU 16e.

If the signal transmitted from the CCD 16a exceeds said slice level, the CPU 16e outputs the information related to the edge of the production label to the main controller 7.

The main controller 7 controls the operation of the driving roller 12 such that the edge of the label L continuously supplied by the label printer 11 is matched with the edge of the production label L2 on the basis of the information related to the diameter of the blood-sampling tube (a) positioned in the label pasting position X and the information related to the edge of the production label detected by the bar-code reader 16.

Figure 8:
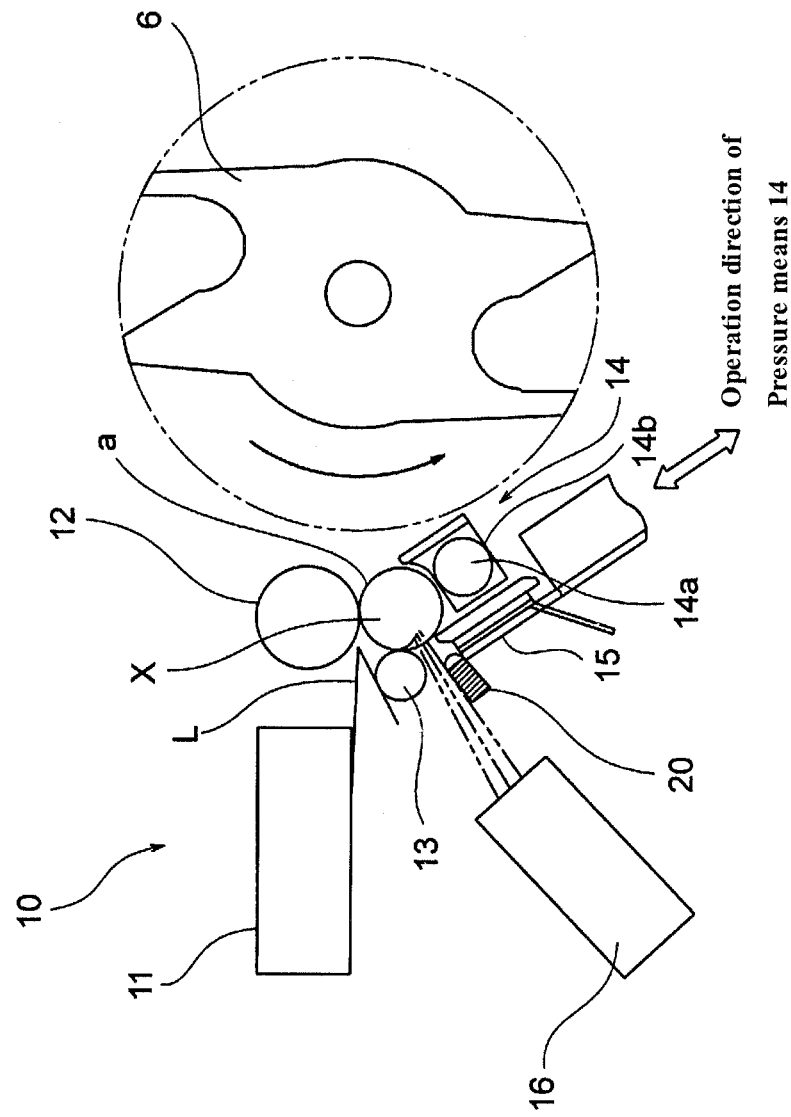
FIG. 8 schematically shows another embodiment of the labeling machine.

As described above, since the labeling machine according to the present invention detects the edge of the production label L2 using the bar-code reader intended to use for checking the identification label L pasted on the blood-sampling tube, it has the advantage that the sensor which detects the edge of the production label L2 specially is not needed, and that structure is not complicated. However as for the labeling machine according to the present invention, it is needless to say that sensor for exclusively detecting the edge of the production label L2 may be provided, without being limited to the above-mentioned embodiments (See FIG. 8). The labeling machine shown in FIG. 8 is the same structure as the labeling machine shown in FIG. 2 except providing the sensor 20 which exclusively detects the edge of the production label L2.

In the above mentioned embodiments, the sampling and holding circuit picks out the signal corresponding to the data picking out area information from the scanned signal regardless of direction of the blood-sampling tube at the label pasting position X. However it is possible that according to the direction of the blood-sampling tube the data picking out area information may be sifted along the axis direction of the blood-sampling tube.

In the above mentioned embodiments, the labeling machine according to the present invention carries out the edge detection process for the all blood-sampling tube supplied to the label pasting position X regardless of the existence of the production label L2. However it is possible that for example the information related to the existence of the production label L2 of the blood-sampling tube contained in the each blood-sampling tube containing section 2 may be pre-stored in the main controller 7, the edge detection process may be carried out only for the blood-sampling tube on which the production label L2 has been pasted and may not be performed for the blood-sampling tube on which the production label L2 is not pasted.

In the above mentioned embodiments, the labeling machine detects the longitudinal edge (i.e. the edge parallel to the direction of axis of the blood-sampling tube) of the production label L2 pasted on the blood-sampling tube and pastes the identification label L so as to match the longitudinal edge of the identification label L with the longitudinal edge of the production label L2. However as for the labeling machine according to the present invention, the labeling machine may detect the transverse edge (i.e. the edge being perpendicular to axis of the blood-sampling tube) as well as the longitudinal edge of the production label L2 and may paste the identification label L so as to match the longitudinal edge and transverse edge of the identification label L with the longitudinal edge and transverse edge of the production label L2. Thereby, it becomes possible to secure the transparent area of the blood-sampling tube more widely, and visibility improves further.

DESCRIPTION OF THE REFERENCE NUMERAL a blood-sampling tube
L identification label
L2 production label
X label pasting position
D clearance gap
1 blood-sampling tube automatic preparation device
2 blood-sampling tube containing section
4 discharging part
5 collecting means
5a containing means
6 blood-sampling tube supplying means
7 main controller 10 labeling machine
11 label printer
12 driving roller
13 support roller
14 pressure means
14a pressure roller
14b pressure rack
15 guide part
16 bar-code reader
16a CCD
16b low-pass filter
16c sampling and holding circuit
16d A/D converter
16e CPU
20 edge exclusive detection sensor

What is claimed is:

1. A labeling machine for a blood-sampling tube automatic preparation device which selectively automatically picks up a blood-sampling tube required for the examination of the patient from blood-sampling tube containing sections on the basis of an information related to one patient that includes examination information, patient information, or both, prints the examination information, patient information, or both on a label on the basis of said information related to one patient so as to make an identification label, pastes the identification label on the blood-sampling tube picked up from the blood-sampling tube containing sections, and collects the blood-sampling tube on which the identification label is pasted into a container for every patient, characterized in that said labeling machine comprises:
   a supporting means for supporting the blood-sampling tube that is picked up on the basis of the information related to one patient at a label pasting position;
   a blood-sampling tube driving means for rotating the blood-sampling tube at the label pasting, position;
   a label printing means for printing the examination information, patient information, or both on the label on the basis of the information related to one patient to make an identification label and for outputting the identification label to the label pasting position;
   a production label position detection means for detecting an edge of a production label pre-pasted on the surface of the blood-sampling tube at the label pasting position; and
   a control means for controlling the operations of the label printing means and the blood-sampling tube drive means so as to paste the identification label on the production label remaining a clearance gap continuously extended along the axis direction of the blood-sampling tube on the surface of the blood-sampling tube on the basis of a diameter information of the blood-sampling tube at the label pasting position and the edge information of the production label detected by the production label position detection means.

2. The labeling machine as claimed in claim 1 characterized in that said control means is a controller for also controlling the operation of the blood-sampling tube automatic preparation device.

3. The labeling machine as claimed in claim 1 characterized in that said control means comprises a memory in which the diameter information of each of the blood-sampling tubes is stored.

4. The labeling machine as claimed in claim 1 characterized in that said control means receives the diameter information of each of the blood-sampling tubes from a host computer.

5. The labeling machine as claimed in claim 1 characterized in that:
   the labeling machine further comprises a measuring means for measuring the diameter of the blood-sampling tube at the label pasting position; and
   said control means receives the diameter information of each of the blood-sampling tubes from said measuring means.

6. The labeling machine as claimed in claim 1 characterized in that:
   the labeling machine further comprises a bar-code reader for checking the identification label pasted on the blood-sampling tube; and
   said production label detection means consists of said bar-code reader.

7. The labeling machine as claimed in claim 6 characterized in that:
   said bar-code reader comprises an optical scanning means for scanning an external surface of the blood-sampling tube along the axis direction of the blood-sampling tube;
   said optical scanning means scans the external surface of the blood-sampling tube several times over one turn of the blood-sampling tube while the blood-sampling tube is rotated at the label-pasting position by means of the blood-sampling tube driving means;
   the bar-code reader calculates an average of each scanned signal for one turn of the blood-sampling tube, and makes a data row containing calculated data for one turn of the blood-sampling tube; and
   the bar-code reader calculates each of differences between two continuous data of the data row and detects a position corresponding to the two continuous data in which the difference becomes the maximum as the edge of the production label.

8. The labeling machine as claimed in claim 6 characterized in that:
   said bar-code reader comprises an optical scanning means for scanning an external surface of the blood-sampling tube along the axis direction of the blood-sampling tube;
   said optical scanning means scans the external surface of the blood-sampling tube several times over one turn of the blood-sampling tube while the blood-sampling tube is rotated at the label-pasting position by means of the blood-sampling tube driving means;
   the bar-code reader calculates an average of the each scanned signals for one turn of the blood-sampling tube, makes a data row containing calculated data for one turn of the blood-sampling tube, and makes a histogram of the data row; and
   the bar-code reader detects the edge of the production label on the basis of the histogram.

9. The labeling machine as claimed in claim 6 characterized in that
   said bar-code reader comprises an optical scanning means for scanning an external surface of the blood-sampling tube along the axis direction of the blood-sampling tube;
   said optical scanning means scans the external surface of the blood-sampling tube several times over one turn of the blood-sampling tube while the blood-sampling tube is rotated at the label-pasting position by means of the blood-sampling tube driving means;
   the bar-code reader calculates an average of the each scanned signal for one turn of the blood-sampling tube, makes a data row containing calculated data for one turn of the blood-sampling tube, calculates an average of the data row, and sets the average of the data row as a slice level; and
   the bar-code reader detects the edge of the production label on the basis of the slice level.

* * * * *